US006491649B1

(12) United States Patent
Ombrellaro

(10) Patent No.: US 6,491,649 B1
(45) Date of Patent: Dec. 10, 2002

(54) DEVICE FOR THE DIRECT MANUAL EXAMINATION OF A PATIENT IN A NON-CONTIGUOUS LOCATION

(76) Inventor: Mark P. Ombrellaro, 5708 - 145th Ave. SE., Bellevue, WA (US) 98006

(*) Notice: Subject to any disclaimer, the term of this patent is extended or adjusted under 35 U.S.C. 154(b) by 120 days.

(21) Appl. No.: 09/685,327

(22) Filed: Oct. 6, 2000

(51) Int. Cl.$^7$ ............................ A61B 5/103; A61B 5/117
(52) U.S. Cl. ...................................................... 600/587
(58) Field of Search ................................ 600/587, 300, 600/595, 552, 553, 554, 555; 341/20; 345/161, 145, 168, 157, 156; 128/903, 904; 434/275

(56) References Cited

U.S. PATENT DOCUMENTS

| | | |
|---|---|---|
| 3,428,747 A | 2/1969 | Alferieff |
| 3,742,935 A * | 7/1973 | Baessler et al. ............ 434/275 |
| 3,791,375 A | 2/1974 | Pfeiffer |
| 3,974,491 A | 8/1976 | Sipe |
| 4,074,444 A | 2/1978 | Laenger, Sr. et al. |
| 4,296,756 A | 10/1981 | Dunning et al. |
| 4,337,780 A | 7/1982 | Metrick |
| 4,414,537 A | 11/1983 | Grimes |
| 4,426,884 A | 1/1984 | Polchaninoff |
| 4,444,205 A | 4/1984 | Jackson |
| 4,492,234 A | 1/1985 | Arkans |
| 4,503,705 A | 3/1985 | Polchaninoff |
| 4,524,348 A | 6/1985 | Lefkowitz |
| 4,586,387 A | 5/1986 | Morgan et al. |
| 4,715,235 A | 12/1987 | Fukui et al. |
| 4,852,443 A | 8/1989 | Duncan et al. |
| 4,967,764 A | 11/1990 | Basser |
| 4,986,280 A | 1/1991 | Marcus et al. |
| 4,988,981 A | 1/1991 | Zimmerman et al. |
| 5,047,952 A | 9/1991 | Kramer et al. |
| 5,060,527 A | 10/1991 | Burgess |
| 5,086,785 A | 2/1992 | Gentile et al. |
| 5,119,831 A | 6/1992 | Robin et al. |
| 5,166,462 A | 11/1992 | Suzuki et al. |
| 5,181,522 A | 1/1993 | McEwen |
| 5,271,412 A | 12/1993 | Shtalryd et al. |
| 5,316,017 A | 5/1994 | Edwards et al. |
| 5,339,821 A | 8/1994 | Fujimoto |
| 5,375,397 A | 12/1994 | Ferrand et al. |
| 5,381,158 A | 1/1995 | Takahara et al. |

(List continued on next page.)

*Primary Examiner*—Kevin Shaver
*Assistant Examiner*—Brian Szmal
(74) *Attorney, Agent, or Firm*—Christensen O'Connor Johnson Kindness PLLC

(57) ABSTRACT

A device is disclosed that enables a physician to remotely perform a physical examination of a patient. The device includes a hand control unit (100) that is shaped to accommodate a physician's hand, and includes a number of sensory modulation subunits (140) that can simultaneously detect applied pressure and exert pressure back to the physician. The hand control unit (100) connects through a computer (160) to a remote patient examination module (200). The patient examination module (200) interfaces with a remotely located patient, preferably by wrapping around the portion of the patient's body that is to be examined. The patient examination module (200) includes a plurality of sensory modulation subunits (240) arranged in an array forming a flexible pad (202). In operation the sensory modulation subunits (240) of the patient examination module (200) receive a signal from the hand control unit (100) that indicates the location and magnitude of pressure's applied to the hand control unit (100) by the physician, and replicates that pressure in the patient through the sensory modulation subunits (240), which simultaneously detect the responsive pressures exerted by the corresponding portions of the patient's body. The magnitude and location of these responsive pressures are converted to a digital signal that is fed back to the hand control unit (100) sensory modulation subunits (140), providing the physician with a tactile response simulating direct contact with the patient.

30 Claims, 11 Drawing Sheets

U.S. PATENT DOCUMENTS

| | | | | |
|---|---|---|---|---|
| 5,381,805 | A | 1/1995 | Tuckett et al. | |
| 5,429,140 | A | 7/1995 | Burdea et al. | |
| 5,444,462 | A | 8/1995 | Wambach | |
| 5,448,996 | A | 9/1995 | Bellin et al. | |
| 5,449,002 | A | 9/1995 | Goldman | |
| 5,509,810 | A | 4/1996 | Schertz et al. | |
| 5,513,651 | A | 5/1996 | Cusimano et al. | |
| 5,515,865 | A | 5/1996 | Scanlon | |
| 5,533,531 | A | 7/1996 | Edwards et al. | |
| 5,555,894 | A | 9/1996 | Doyama et al. | |
| 5,562,707 | A | 10/1996 | Prochazka et al. | |
| 5,581,484 | A | 12/1996 | Prince | |
| 5,589,639 | A | 12/1996 | D'Antonio et al. | |
| 5,662,121 | A | 9/1997 | Zucker | |
| 5,676,157 | A | 10/1997 | Kramer | |
| 5,697,165 | A | 12/1997 | Richardson | |
| 5,715,834 | A | 2/1998 | Bergamasco et al. | |
| 5,764,164 | A | 6/1998 | Cartabiano et al. | |
| 5,771,492 | A | 6/1998 | Cozza | |
| 5,775,332 | A | 7/1998 | Goldman | |
| 5,778,885 | A | 7/1998 | Doyama et al. | |
| 5,813,406 | A | 9/1998 | Kramer et al. | |
| 5,817,030 | A | 10/1998 | Tarjan et al. | |
| 5,826,578 | A | 10/1998 | Curchod | |
| 5,833,633 | A | 11/1998 | Sarvazyan | |
| 5,838,244 | A | 11/1998 | Schmidt et al. | |
| 5,852,258 | A | 12/1998 | Tribou | |
| 5,911,693 | A | 6/1999 | Prochazka et al. | |
| 5,916,180 | A | 6/1999 | Cundari et al. | |
| 5,929,782 | A | 7/1999 | Stark et al. | |
| 5,964,719 | A | 10/1999 | Costello et al. | |
| 5,964,720 | A | 10/1999 | Pelz | |
| 5,982,352 | A | 11/1999 | Pryor | |
| 5,984,880 | A * | 11/1999 | Lander et al. | 600/595 |
| 5,986,643 | A | 11/1999 | Harvill et al. | |
| 5,989,199 | A | 11/1999 | Cundari et al. | |
| 6,004,312 | A | 12/1999 | Finneran et al. | |
| 6,030,347 | A | 2/2000 | Nakamura et al. | |
| 6,033,370 | A | 3/2000 | Reinhold et al. | |
| 6,035,274 | A | 3/2000 | Kramer et al. | |
| 6,036,660 | A | 3/2000 | Toms | |
| 6,042,555 | A | 3/2000 | Kramer et al. | |
| 6,047,259 | A | 4/2000 | Campbell et al. | |
| 6,049,327 | A | 4/2000 | Walker et al. | |
| 6,050,962 | A | 4/2000 | Kramer et al. | |
| 6,184,868 | B1 * | 2/2001 | Shahoian et al. | 345/156 |
| 6,186,962 | B1 * | 2/2001 | Lloyd et al. | 600/587 |
| 6,259,382 | B1 * | 7/2001 | Rosenberg | 341/20 |
| 6,310,604 | B1 * | 10/2001 | Furusho et al. | 345/156 |

* cited by examiner

DEVICE FOR THE DIRECT MANUAL EXAMINATION OF A PATIENT IN A NON-CONTIGUOUS LOCATION

FIELD OF THE INVENTION

This invention relates to medical devices that transmit tactile information from a remote location to an individual and, in particular, to devices that assist in the examination of a patient at a location remote from the location of a medical examiner.

BACKGROUND OF THE INVENTION

Computer technology and the enhanced ability for individuals to communicate via the Internet and other wide area networks have greatly altered our society. These communications platforms have allowed for the effective and efficient worldwide transfer of data as well as accessibility of this information to the general public. The way in which people communicate, exchange information, and transact business is being substantially affected by these developments. Traditional business practices are being expanded such that any business with a computer and Web site has potential access to any consumer in the world with a computer. Each individual business now has essentially a worldwide customer base. While many businesses are capitalizing on these current trends, the health care industry is one notable exception that is substantially lagging.

The health care environment is extremely complex. While third party and government payers and players in this arena have applied pressure to patients, hospitals, and physicians in order to "standardize" health care issues into predictable business models, this has been a difficult task to date. The uniqueness of each individual and the underlying basic characteristics of biological organisms, in themselves, preclude medicine from ever being an exact science which can be accurately predicted in all respects. This variability among patients, their diseases, their individual manifestation of similar diseases, and physician skill, training, and treatment practices all contribute to the difficulty in standardizing medical information collection, data storage, treatment algorithms, outcomes, and business modeling.

Medical practice is also a very unique type of personal service. A sick patient interacts with a unique skilled professional with the expectation of improving his or her health condition or alleviating suffering. The underlying physician-patient encounter is in actuality a complex data gathering interaction which is processed by the physician, who then develops an optimal diagnosis and treatment plan. The input data from the physician-patient encounter comes from a variety of sources which include the physical examination of the patient, laboratory tests, and radiological imaging studies, The most important source of input information is often the actual physical examination of the patient. The physical examination consists of the transfer of personal historical information from the patient to the physician, a review of the patient's current medications, and a direct visual and manual examination of the patient's body by the physician.

The manual examination of the patient's body includes applying gentle hand pressure along various parts of the abdomen, chest, and extremities in order to determine the body's response to direct manipulation. Inflammatory processes such as infections, abscesses, thromboses (clots), hollow or solid organ perforations, or fractures will yield a pain response with an increase in resistance in order to "guard" or protect against the noxious applied stimulus. Tumors or organ enlargement may be detected by resistance changes detected below an otherwise normal skin surface, analogous to perceiving a stone trapped in one's shoe. Fluid within the abdomen (ascites) can also be detected by applying hand pressure at one end of the abdomen and detecting the resultant fluid wave at an opposite location within the same cavity.

An expertly performed history and physical examination will yield a correct diagnosis with approximately 90% accuracy. In most circumstances, the laboratory and radiological imaging data provide confirmation of the diagnosis as well as adjunctive detail regarding the patient's condition. In the general sense, the physician functions as a computer by collecting all of the available input data from the various sources, processing that information with respect to the physician's personal knowledge or reference base, and establishing a list of likely diagnostic possibilities based on the input information. The physician then recommends a plan of treatment which is expected to improve the patient's health condition.

A portion of the data required to make an accurate medical diagnosis can be exchanged between the patient, laboratory, radiology, and physician using a variety of communications methods without the need for direct face to face contact between the communicating entities. The current communications revolution has allowed for the exchange of historical information, laboratory data, telemetry, and radiological studies via telephone, pager, fax, e-mail, and video. These advances have benefited all types of businesses, and medicine is no exception. There is, however, one unique piece of the data gathering process specific to medicine—the direct manual examination of the patient's body by the physician—which currently is not amenable to remote data acquisition.

SUMMARY OF THE INVENTION

The present invention provides a system satisfying the needs identified above. The device includes a hand control unit, a remote examination module, and a computer system connecting the hand control unit to the remote examination module. The present invention relates generally to a system enabling a user to send tactile stimuli such as a pressure input to a remote body such that the stimuli is experienced by the remote body to produce a response, detect the tactile response of the remote body to generate feedback, and transmit that tactile feedback to the user. A preferred embodiment of the invention is directed to remote patient examinations, and includes a physician's hand control unit (HCU) that is used by a physician to generate tactile stimuli, and is coupled by a computer system to a patient examination module (PEM) that applies the tactile stimuli to a patient and detects and transmits feedback corresponding to the detected response back to the HCU.

The HCU has at least one and preferably a plurality of sensory modulation subunits, and is adapted to receive the physician's hand such that the physician has access to the sensory modulation subunits. The PEM is adapted to contact or receive a portion of a patient's anatomy, preferably by wrapping around a portion of the patient, and has at least one and preferably a plurality of sensory modulation subunits that are thereby placed adjacent to the patient. The sensory modulation subunits detect forces or pressures applied to the subunits to produce corresponding output signals, and exert forces and/or displacements in response to input signals. Preferably, detection and exertion of forces occur approximately simultaneously. The sensory modulation subunits in the HCU are coupled to the sensory modulation subunits on the PEM through the computer system. In one embodiment, the computer system includes a first computer attached to the HCU and a second computer attached to the PEM, wherein the first and second computers have compatible communication systems to enable communications therebetween over a network.

The sensory modulation subunits on the HCU are coupled to the sensory modulation subunits on the PEM through software that feeds back the pressures detected, which permits the physician to simulate actual physical contact with a remote patient.

In a first preferred embodiment of the device, the PEM utilizes sensory modulation subunits with mechanical piston-type variable pressure-producing devices, such as linear actuators, to exert pressure in response to input signals. In a second embodiment of the device, the PEM utilizes pneumatic or hydraulic systems and expandable cells to produce the exerted pressure in response to input signals.

In an aspect of the present invention, the HCU includes a tracking ball and a button accessible to the user's hand which allows the physician to use the HCU in a manner similar to a computer mouse to interact with the computer-for example, to select specific portions of the PEM with which to interface.

BRIEF DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein.

DETAILED DESCRIPTION OF THE PREFERRED EMBODIMENT

The device disclosed herein enables a physician to perform a direct physical examination of a patient's body without direct physical contact or proximity between the patient and the physician. This allows physical data of the type normally acquired from direct manual contact between the patient and the physician to be gathered and transmitted via conventional global communications systems. To date, "telemedicine" or the exchange of medical information between a patient and physician for the purpose of rendering a diagnosis and treatment plan, can only proceed to a point, and if the physical exam findings become critical in the decision making process, the patient is advised to actually see their personal physician or present to an emergency room where a physician can perform a physical examination. This inability to acquire physical data remotely and transfer it reliably to a physician in another location is a barrier to the evolution of medical practice and the ability of medicine to capitalize on the effectiveness and efficiencies that other business are enjoying with respect to the advances in global communications platforms and a potential global consumer audience.

As used herein, the following terms shall have the meaning indicated:

Sensory modulation subunit means any device capable of (1) detecting a force applied to the device and generating an output signal related to the detected force; and (2) receiving an input signal and generating a force and/or displacement related to the received input signal.

Hand control unit, or HCU, means any device adapted to contact or receive a portion of a user's body—such as a user's hand—and having sensory modulation subunits that can be accessed by the received user's hand.

Patient examination module, or PEM, means any device adapted to receive a portion of a person's (or other biological organism's) anatomy, and having sensory modulation subunits that are adjacent to the received portion of anatomy. PEMs may be used in accordance with the present invention for patient examination, but the term PEM is to be understood to also encompass devices adapted for tactile sensing of anatomy for other purposes, or for tactile sensing of other objects or substances.

Figure 1:
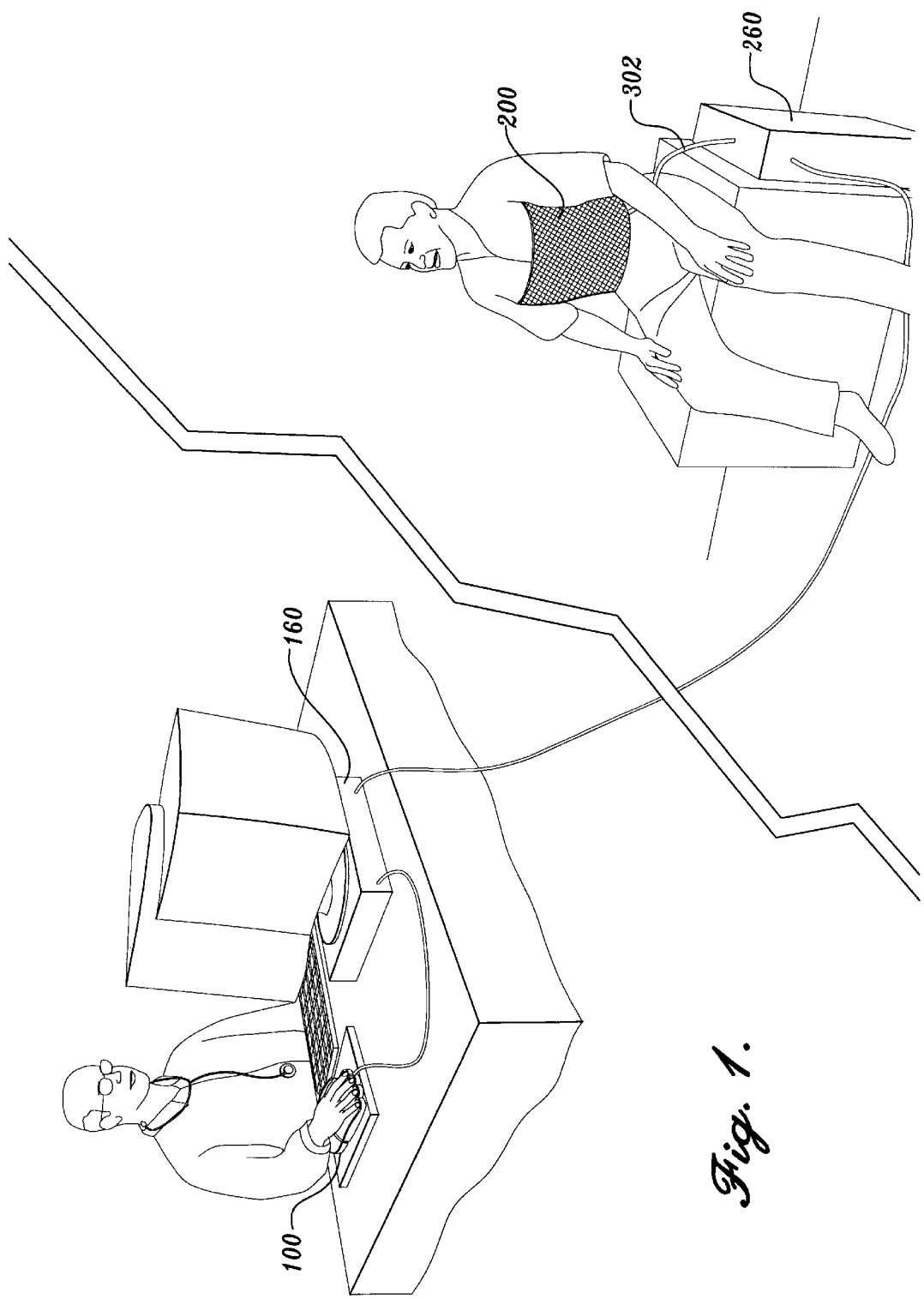
FIG. 1 illustrates a preferred embodiment of the system of the present invention in use, showing a physician examining a patient who is located remotely from the physician.

Referring now to FIG. 1, the present invention, for the remote acquisition and transmission of physically derived medical data, includes three general parts: the hand control unit 100 (HCU), the patient examination module 200 (PEM), and computer software to control the acquisition, calibration, transfer, and translation of the physical data between the physician (through the HCU) and the patient (through the PEM). The present invention allows a physician to apply hand pressures to the HCU 100 that are transmitted to a remotely situated patient and applied to selected portions of the patient's body through the PEM 200. The pressure response from the patient's body is transmitted back to the physician, thereby simulating direct contact between the physician and patient.

Hand Control Unit (HCU)

Figure 2:
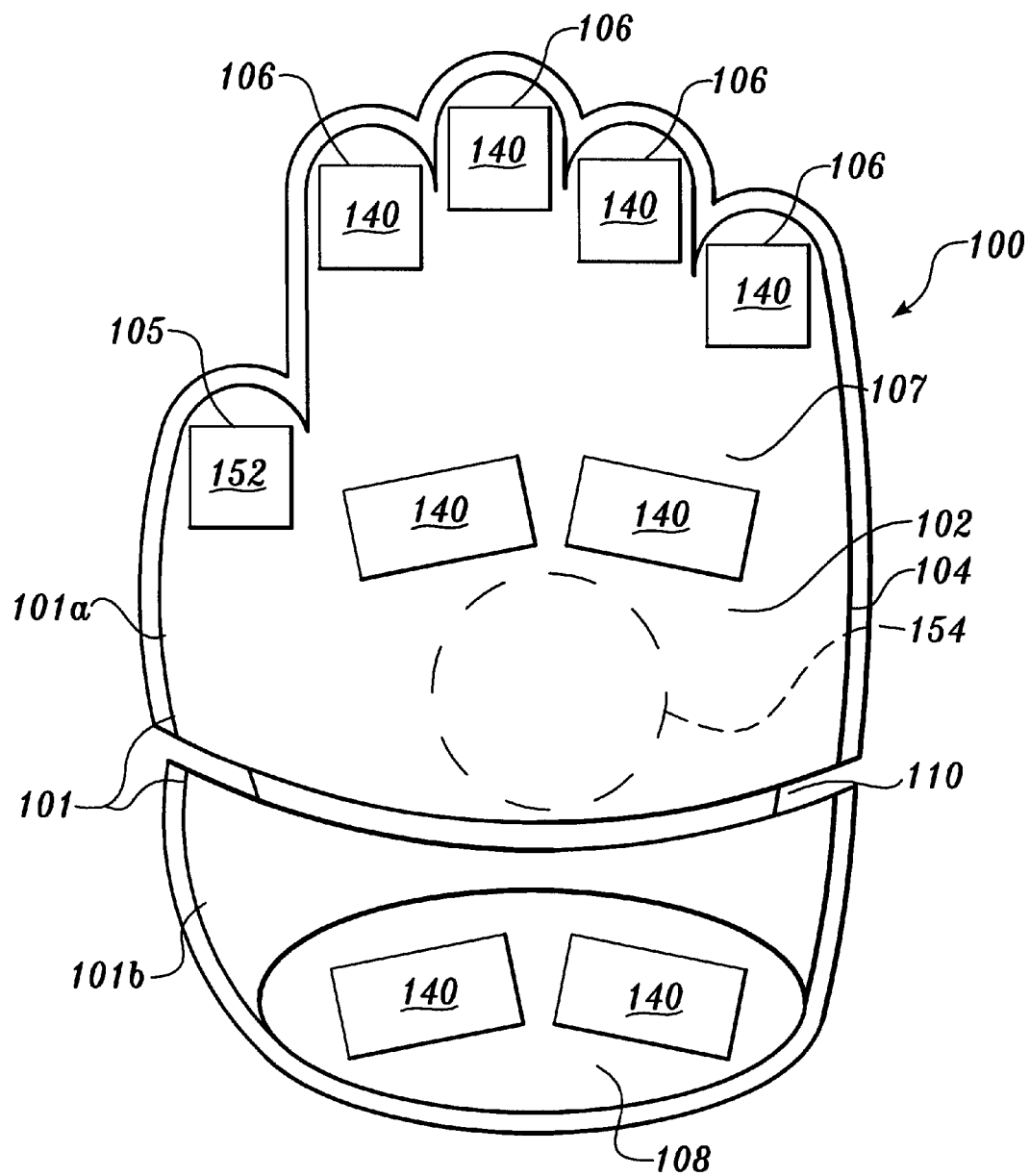
FIG. 2 is a plan view of a hand control unit in accordance with the present invention.

The HCU 100, shown in FIG. 2, has a molded plastic shell 101 formed in the shape of an actual hand. The advantages of this type of construction are that it is lightweight, easy to manufacture, durable, and impact resistant. Other materials such as wood, paper, aluminum, stone, PlexiglasTM, or as of yet to be developed materials could also be used for device construction. The HCU 100 is shaped to accommodate a portion or preferably the entire inner surface of the human hand, having a palmar surface 102 including a proximal palm portion 108 and a distal palm portion 107, fingertips 106, and a thumb portion 105. An objective of any design configuration is to provide a comfortable contact surface between sensory and motor portions of the user's hand and the HCU 100. In the preferred embodiment, the HCU 100 has a slight central rise in the palmar surface 102. The periphery of the palmar surface 102 has a slight depression with respect to a border 104 of the HCU 100 to accommodate the user's hand resting comfortably on the palmar surface 102. The slight palmar rise with respect to the position of the fingertips 106 and proximal palm portion 108 (such that the level of the user's knuckles will be higher than the other parts of the fingers and hand) forms a broad based, pyramidal configuration. This design allows for maximum flexibility with respect to fingertips, distal palm, and proximal palm pressure application and reception, device control, and functionality. The HCU 100 allows for complete contact between all parts of the palmar surface of the user's palm and fingers with the palmar surface 102 of the HCU 100. In the preferred embodiment, the shell 101 of the HCU 100 is formed in two laterally disposed segments 101a, 101b, with a transverse break 110 located generally at the location of the user's mid-palmar crease. The two segments 101a, 101b, are slidably connected to permit relative longitudinal motion to allow for adjustments with respect to hand length in order to accommodate various hand sizes. Optionally, the HCU 100 could include a "glove" component (not shown) where the whole hand is inserted into a hand control unit. This would allow for contact with the top (dorsal) hand surface permitting functions related to examination motions and sensory inputs derived from the top surface of the operator's hand.

Figure 3:
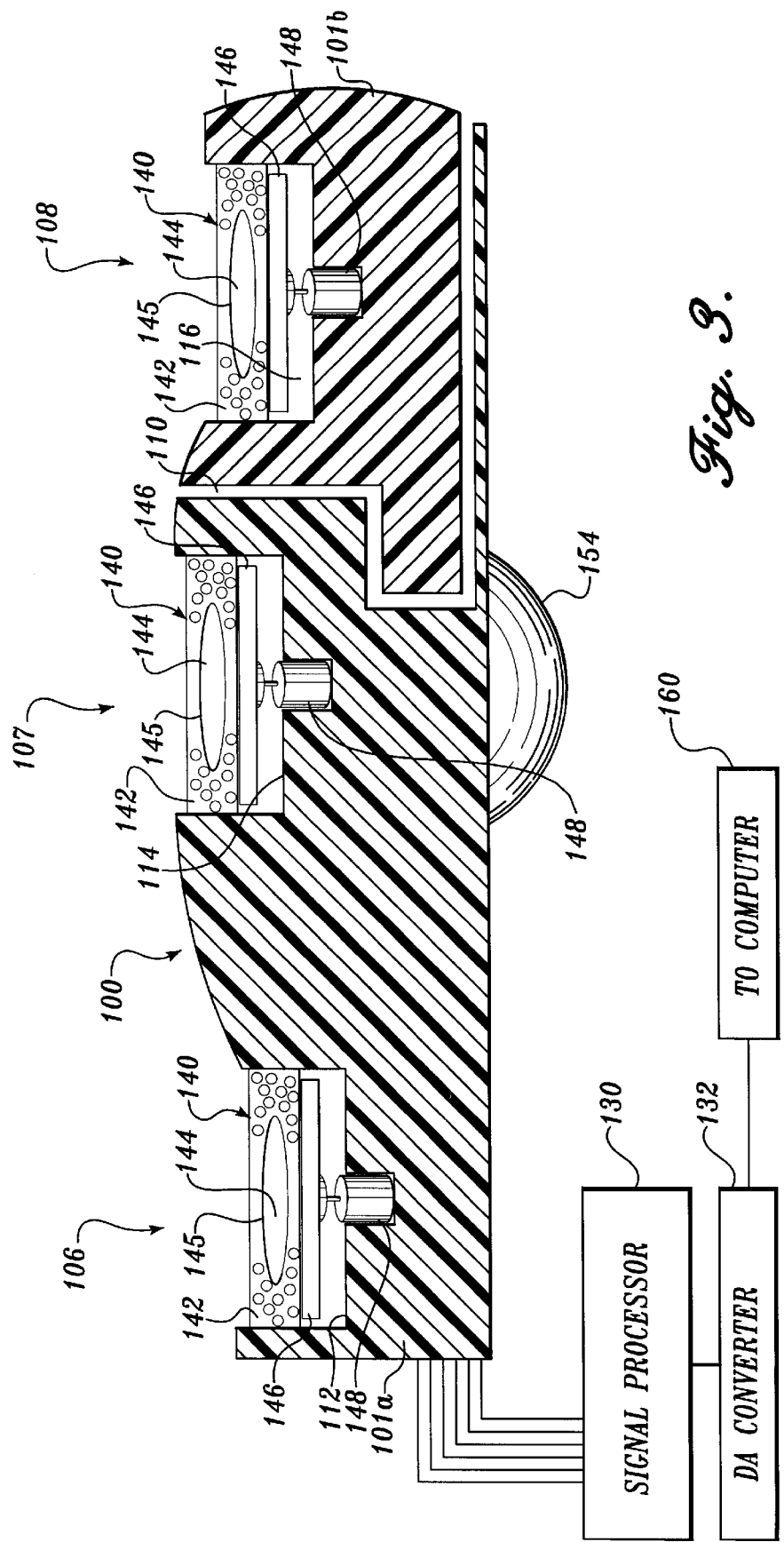
FIG. 3 is a schematic cross-sectional view of the hand control unit of FIG. 2.

Depressions or cavities 112, 114, 116, are provided in the fingertips 106, distal palm 107, and proximal palm portions 108, respectively. Within each depression 112, 114, 116, a pressure relay and reception sensory modulation subunit 140 is housed, as seen most clearly in FIG. 3. The top of the sensory modulation subunit 140 consists of a slab 142 of a pliable material such as silicon rubber or a soft plastic matrix forming a simulated skin surface. Other suitable materials may include other natural or artificial biomaterials (artificial, simulated, cultured, or engineered skin cells or substitutes) for this "skin" contact surface. The size of each slab 142 will vary with the size of each depression 112, 114, 116 in the HCU 100. In general, there are fingertip-sized sensory modulation subunits 140 for each of the fingertip 106 areas of the device, a proximal palm-sized subunit 140, and a distal palm-sized subunit 140 for the proximal palm 108 and distal palm 107 portions, respectively. To increase the sensitivity and functionality of the HCU 100, each module could be multiply subdivided and each depression could include a collection of smaller functional subunits based on the general subunit description below.

Figure 4:
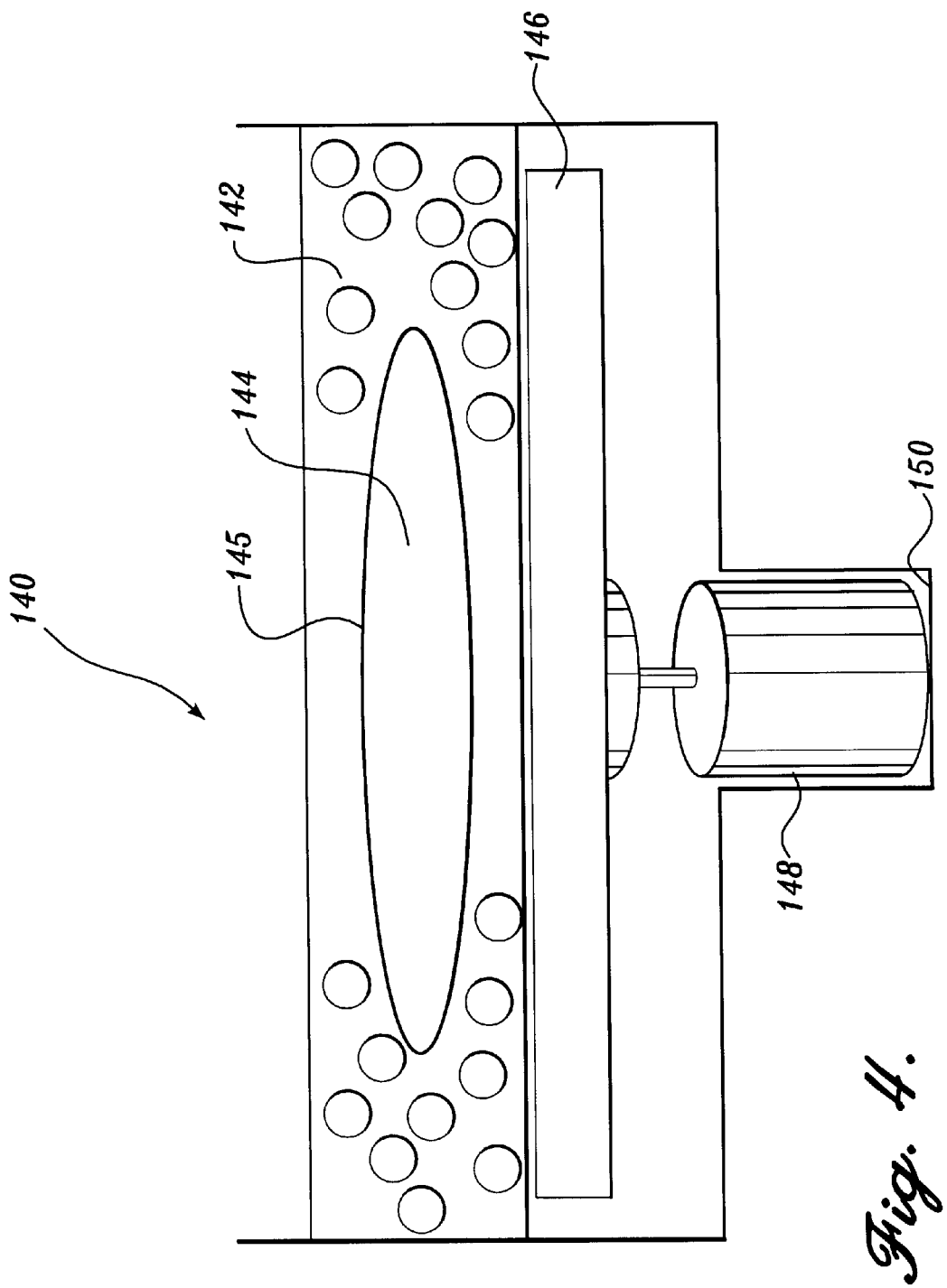
FIG. 4 is a cross-sectional sketch of a sensory modulation subunit for the hand control unit shown in FIG. 3, in accordance with the present invention.

Referring now to FIG. 4, the sensory modulation subunit 140 includes a one-way single channel pressure transducer 144 embedded within the slab 142 of simulated skin. The working surface or pressure receiving face 145 of the pressure transducer 144 is oriented upward, i.e., in the direction facing the palmar surface of the user's hand. The pressure transducer 144 is oriented such that pressure applied by the user is applied to the working surface 145 of the pressure transducer 144, while pressure or force applied from behind the transducer 144 is not sensed directly. In the preferred embodiment, a single pressure transducer 144 is located within each fingertip 106, while each palmar portion 107, 108, is subdivided into two pressure zones. Wires or other appropriate connecting mechanism (not shown) provide signal access to and from the pressure transducer 144.

The simulated skin slab 142 with the embedded single channel pressure transducer 144 is mounted on a thin support platform 146, preferably made of metal or plastic. Attached to the undersurface of the support platform 146 is a linear actuator, a variable force-producing device such as a single channel piston-type variable resistor, or other variable pressure-producing device 148. The linear actuator, or variable pressure-producing device 148, referred to herein as the "piston resistor," may be embodied in a number of ways that are known in the art, including devices that produce a variable force by electrical, mechanical, pneumatic, or hydraulic processes. A representative sampling of such devices are described, for example, in U.S. Pat. No. 5,631,861 to Kramer, illustrated in FIGS. 8a–m thereof, and referred to therein as a "finger tip texture simulator." In the preferred embodiment of the present invention, magnetically motivated devices are utilized. The piston resistor 148 provides counter pressure or a resistance force against the undersurface of the simulated skin slab 142 dependent upon the response signal derived from the patient examination module 200 (described below). The slab 142, transducer 144, support platform 146, and piston resistor 148 are disposed within the depressions 112, 114, 116, in the HCU 100. Holes 150 are provided within each depression 112, 114, 116, to accommodate insertion of the free end of the piston resistor 148. The hole 150 depth is selected such that the support platform 146 is slightly elevated from the depression lower surface and therefore the only resistance felt by the user is that of the simulated skin slab 142 itself.

Various types of pressure transducers are known in the art and suitable for use in the present invention. For example, and without limiting the scope of the present invention, U.S. Pat. No. 6,033,370 issued to Reinbold et al., discloses a capacitive pressure force transducer having a polyurethane foam dielectric sandwiched between two conductor layers. A similar device is disclosed by Duncan et al. in U.S. Pat. No. 4,852,443, wherein compressible projections on the capacitor electrodes are disposed on either side of a dielectric sheet. A pressure transducer based on variable resistance components is disclosed in U.S. Pat. No. 5,060,527 by Burgess.

Referring again to FIG. 2, the corresponding thumb portion 105 of the HCU 100 houses a button 152 for controlling and selecting functions and options related to the computer software (e.g., a mouse click control or other input device). The under surface of the HCU 100 supports a tracking ball 154 to allow for computer selection functions, and two-dimensional coordinate location of the HCU 100 in space as related to the patient through the PEM 200. It will be apparent to one of skill in the art that the button 152 and tracking ball 154 provide the basic functionality of a computer mouse and can be used to selectively interact with the computer in a familiar and well-known manner. It will also be apparent that other types of selecting mechanisms could be utilized, including touch-sensitive pads and optical systems. The HCU 100 is also linked to a signal processor 130 and an analog-to-digital/digital-to-analog signal converter 132.

The HCU 100 acts as the interface or contact point between the physician and the remote patient. The HCU 100 receives the mechanically applied pressure signal generated by the physician's hand and converts it to an electrical signal via the pressure transducer 144, while simultaneously converting the incoming electrical signal derived from the pressure response at the patient examination module 200 into a resistance signal that is applied to the piston resistor 148 mounted against the support platform. This ability of the sensory modulation subunit 140 to both "sense" the input pressure applied by the user and simultaneously provide a direct resistance feedback response to the user simulates the actual events that occur when one presses their hand against another object. Higher degrees of resistance sensed by the PEM 200 (actual patient response) in response to the direct pressure applied to the patient (as determined by the input pressure from the HCU 100) is relayed back to the HCU 100 and fed back to the physician through the piston resistor 148. Increasing resistance sensed by the PEM 200 will correspond to increasing force being applied to the undersurface of the support platform 146. This translates into a sensation of greater resistance or a "lack of give" to the simulated skin slab 142. This feedback resistance can be perceived by the user as the direct response from the patient to the forces applied by the physician.

The HCU 100 could optionally incorporate single or multiple multi-channel pressure transducer/resistor devices and/or the absolute change in resistance could be translated back to the physician's hand via the hand controller unit. The thumb portion 105, currently used for software command functions, could alternatively house a sensory modulation subunit 140. The ability to integrate thumb motions into the examination process as well as having sensory input back to this part of the hand would allow for expanded functional capacity and sensitivity of the HCU 100. The most complex embodiment of an HCU would include full contact with every portion of the operator's hand, and a large number of sensory modulation subunits 140 applied throughout the HCU. The number of subunits 140 is limited only by the ability to miniaturize these bidirectional pressure transducing devices. A large number of sensory modulation subunits would allow the user to produce and receive mechanical and sensory inputs from every portion of the operator's hand.

Patient Examination Module (PEM)

Figure 5:
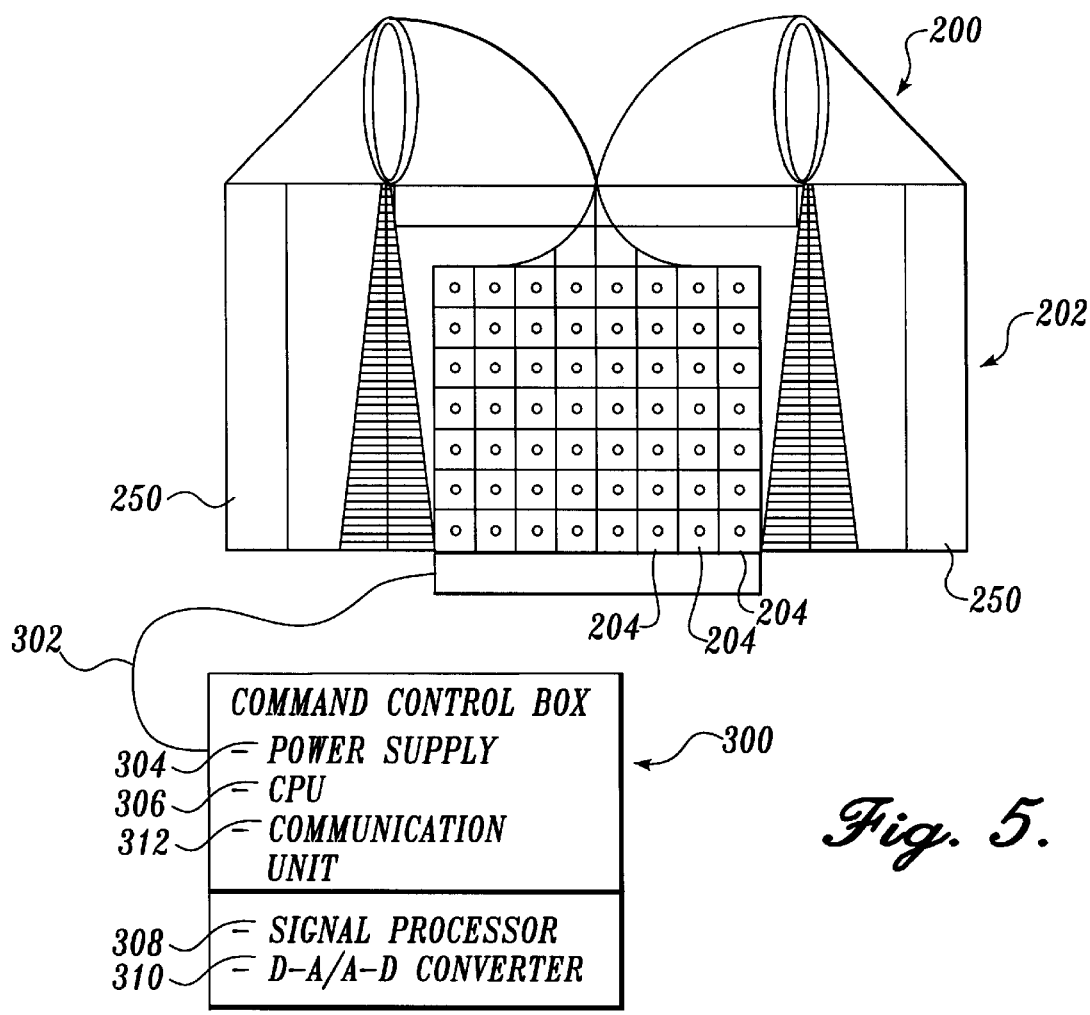
FIG. 5 is a front view of a preferred embodiment of a patient examination module for examination of a patient's torso, in accordance with the present invention.
Figure 6:
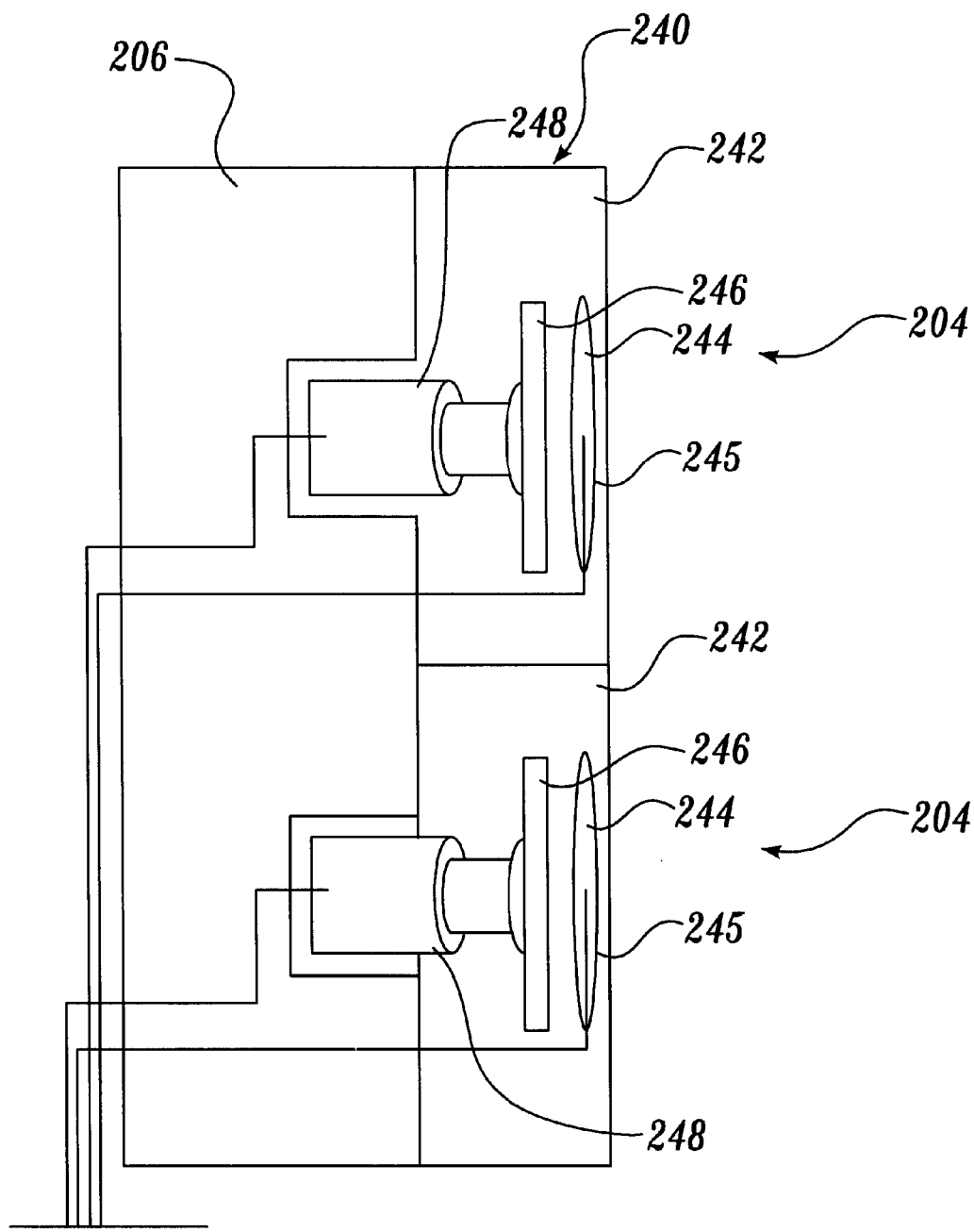
FIG. 6 is a cross-sectional view of a cell from the patient examination module shown in FIG. 5.

Referring now to FIGS. 5 and 6, PEM 200 consists of a pad or pad-like structure 202 made of soft, semi-compliant material such as nylon, rubber, silicon, or a soft plastic substrate. The entire pad 202 is solid, preferably with viscoelastic properties similar to the simulated skin slab 142 of the HCU 100. The pad 202 is subdivided into a basic structural unit called a cell or cell zone 204. The overall size of the pad 202, as well as the number of cells 204 within the pad 202, will vary depending upon the particular application. Each cell zone 204 corresponds to an area within the pad 202, preferably similar in size to the corresponding sensory modulation subunit 140 of the HCU 100. As shown in FIG. 6, a single channel pressure transducer 244 is mounted within each cell 204, oriented with the working/receiving surface 245 facing in the direction of the patient. The preferred pad 202 is a continuous gel-type structure 242 with a multitude of embedded pressure transducers 244. The back surface 206 of the pad 202 includes a flexible, semi-rigid sheeting. The currently preferred material for the back surface 206 is a plastic or polymer substance that will maintain a rigid backing to the cell zones 204, yet allow for some bending to accommodate applications to a variety of body sizes. More solid materials such as metal, wood, or composite materials could also be used as long as it provided a solid backing structure and allowed for articulation around various contoured surfaces of the body. A linear actuator, comprising a single channel piston-type variable pressure producing sensory modulation subunit 240 is attached to the undersurface of a thin support platform 246, preferably made of metal or plastic. The support platform 246 is preferably similar to the size of the fingertips 106 in the HCU 100. Centered directly below each pressure transducer 244 generally located at the interface between the cell 204 and backing 206, a piston-type variable pressure producing device 248, or similar linear actuator is embedded within the backing 206, oriented beneath the center of the support platform 246 below the pressure transducer 244.

The examination pad 202 is applied directly over the portion of the patient's body surface to be examined and held in place, for example, by a nylon loop-and-hook type of closure 250. The nylon loop-and-hook closure 250 would provide adjustability and allow for application to a wide variety of body shapes and sizes. The pad 202 could also be fashioned into vests for chest applications; binders for abdominal applications; sleeves, gauntlets, or gloves for upper extremity applications; pant legs or boots for lower extremity applications; or small strips for small applications such as fingers or toes. While the preferred embodiment of a PEM is constructed as a stationary positioned pad, a mobile sensing unit that the patient, other personnel, or a robotic guide moves over a surface of the patient's epidermis or within a body cavity, is also within the scope of the invention.

In one preferred embodiment, the PEM 200 is attached to a command control box 300 via an electrical umbilical 302. In the preferred embodiment, the command control box 300 includes a power supply 304, a small central processing unit (CPU) 306, a signal processor 308, digital-to-analog converter 310, and a communications system 312, The command control box 300 receives and transmits data to and from the PEM 200, and links the PEM 200 to the physician's HCU 100. The power supply 304 preferably allows for both the ability to work from alternating current (household or industrial) or direct current (battery operations). While an umbilical 302 is illustrated, other data links such as a wireless data link are also within the scope of the invention.

The communications system 312 of the preferred embodiment includes an internal modem (not shown) which would allow a physician's computer 160 located near the HCU 100 to connect to a remote computer 260 located near the PEM 200. Other communication systems are also possible, including systems based on: (1) light-based/optical based communications including fiber-optic cable channels and non-fiber, light based methods of data/voice/visual signal transmission; (2) wireless communications including but not limited to radio frequency, ultrahigh frequency, microwave, or satellite systems in which voice and/or data information can be transmitted or received; and (3) any future methods of voice or data transmission utilizing any currently unused mediums such as infrared light, magnetism, other wavelengths of visible and non-visible radiation, biomaterials (including biorobots or viral vectors), or atomic/subatomic particles. Optimally, the command control box 300 is connected to the pad 202 through a flexible umbilical 302 for considerations of reduced weight being applied directly to the patient, size limitations, and possibly safety (i.e., reduced RF or microwave radiation exposure from communications/data transmissions). The umbilical 302 also connects the pressure transducers 244 and variable pressure producing devices 248 within the sensory modulation subunits 240 to the power supply 304.

Other device configurations could incorporate single or multiple multichannel pressure transducer/resistor devices and the absolute change in resistance could be translated back to the user's hand via the HCU 100. In an attempt to increase the sensitivity and functionality of the PEM 200, each cell zone 204 could be multiply subdivided and a large number of sensory modulation subunits applied throughout the PEM 200. The number of functional subunits would only be limited by the ability to miniaturize these bidirectional sensory modulation subunits. A large number of small sensory modulation subunits would provide the ability to produce and receive mechanical and sensory inputs from every portion of the PEM 200.

Figure 7:
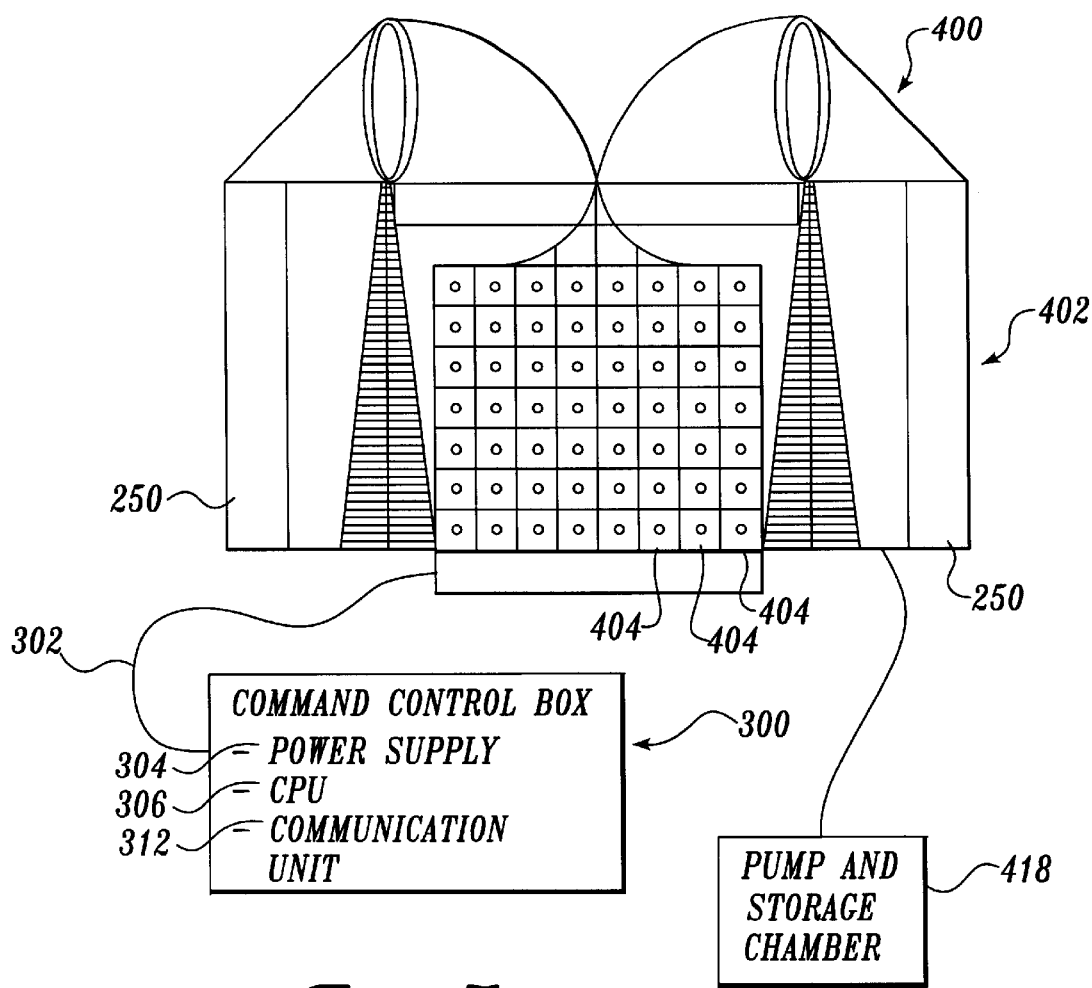
FIG. 7 is a front view of a second preferred embodiment of a patient examination module for examination of a patient's torso, in accordance with the present invention.
Figure 8:
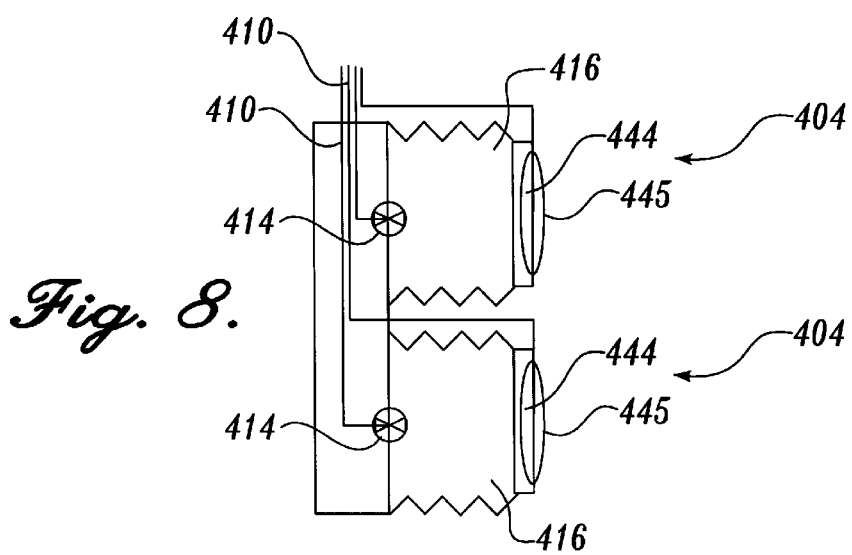
FIG. 8 is a cross-sectional view of a cell from the patient examination module shown in FIG. 7.

A second embodiment of the PEM 400 utilizes a pneumatic pressurizing medium or hydraulic pressurizing medium as shown in FIG. 7 and FIG. 8, rather than the electromechanical structure described above. In this second embodiment, the PEM 400 consists of a pad 402 or pad-like structure made of soft, semicompliant material such as nylon, rubber, silicon, or a soft plastic substrate. The pad 402 is subdivided into a plurality of cells 404. The overall size of the pad 402, as well as the number of cells 404 within the pad 402, will vary by device model and application. Each cell 404 is designed as an air- and water-tight hollow chamber 416 with one dual function inlet/outlet line 410 and one valve 414 to allow inflow and outflow of a pressurizing medium, such as air, water, hydraulic fluid, or an electrochemical gel, and a single pressure transducer 444. The pressure transducer 444 is a single channel transducer similar to the transducer 144 described above for the HCU 100. The pressure transducer 444 is mounted within the material sheet applied directly to the patient's body surface. The open cell structure would therefore be behind the pressure transducer 444. The receiving surface 445 of the transducer would be oriented facing in the direction of the patient.

The pad 402 is applied directly over the portion of the patient's body surface to be examined, and is held in place, for example, by a loop-and-hook type of closure 250. The loop-and-hook closure 250 provides adjustability and allow for application to a wide variety of body shapes and sizes. The pad 402 could also be fashioned into vests, binders, sleeves, gauntlets, gloves, pant legs, boots, or small strips for small applications such as fingers or toes, as previously described. The outer surface of the pad 402 could also include a heavy reinforcing layer (i.e., lead, metal, or plastic) to provide added stability or counter pressure if required. The inlet/outlet line 410 for each cell 404 is connected to a pumping mechanism which would include a pump (not shown) and a pressurizing reservoir 418 for housing the pressurizing medium. An intervening valve 414 is placed along the inlet/outlet line 410 between the pressure reservoir 418 and each cell 404. The PEM 400 is attached to a command control box 300 via an umbilical 302 as previously described.

Preferably this control section of the PEM 400 is disposed away from the patient for considerations of reduced weight being applied directly on the patient, size limitations if the pack is placed on a small section of the body such as a limb or finger, or possibly safety (i.e., reduced RF or microwave radiation exposure from communications/data transmissions). The specifications and functions of the command control box 300 are described above. The umbilical 302 also connects the pressure transducers 444 and the power supply 304, as well as the inlet/outlet lines 410 and valve 414 for the pressurizing medium.

Depending upon the specific HCU 100 design, the pump and pressurizing reservoir 418 could be contained both together in the command control box 300 section, together on the PEM 400 itself, or in either area independent of one another.

A PEM 400 utilizing air as a pressurizing medium would utilize a semiclosed circuit design. In the preferred embodiment, the pumping mechanism draws air from outside the unit into a single pressurizing reservoir 418 applied to the back of the pad 402. The pressurizing reservoir 418 is generally the same size as the pad 402. Valves 414 are located at multiple positions within the pressurizing reservoir 418 corresponding to underlying cells 404. The pressurizing reservoir 418 is therefore in direct communication with each pressure cell 404 via the intervening valve 414. A pressure regulating circuit (not shown) is integrated into the pressurizing reservoir 418 in order to sense internal chamber pressure, and relay that information back to the command control box 300 in order to ensure appropriate chamber pressure. After the appropriate cells 404 are activated, the desired pump chamber pressure achieved (corresponding to the appropriate applied pressure signal from the HCU 100), and the resulting patient response signal is transmitted back to the HCU 100 via the command control box 300, the pump vents the contents of the pressure chamber 416 back into the atmosphere via the pump. A PEM 400 utilizing a hydraulic pressurizing medium consists of a self contained, closed fluid system circuit.

The function of the PEM 400 is to "transmit" the pressure applied by the user at the HCU 100 directly to the patient and send the resultant resistance response signal from the patient back to the physician's HCU 100. Using the software and the physician's HCU 100, various segments of the body within the confines of the PEM 400 can be examined by "selecting" the appropriate overlying cells 404 to be pressurized. The software sends the appropriate command to open the valves 414 corresponding to the selected cells 404. The number of selected cells 404 corresponds to the area of the patient's body the physician wishes to "press on" to elicit the patient's response to the applied "hand" pressure. In addition, the physician can independently select the cells or area of the body from which the return pressure data can be sent back to the user. While in many circumstances the cells which are being pressurized will also be sending the return pressure data signals back to the physician's HCU 100, for some examination functions, it is optimal to pressurize one cell set and receive from a different one.

It is also contemplated that a second HCU could be incorporated, configured to accommodate the hand opposite the first HCU, wherein the physician could use one hand to apply pressure to one location on the patient (through the first HCU and the PEM) and receive a pressure response to the other hand from another location on the patient (through the second HCU).

The computer software controls the commands for the various functions of the physician HCU 100, PEM 200 or 400, system dynamics, and the communications protocols. HCU 100 functions include cell selection functions to activate those specific cells or group of cells to be activated and the cells to transmit the resultant return signals. The software also allows for assignment of specific pressure response pads of the physician HCU 100 to be designated as send patches to transmit the physician's pressure signal as well as receive pads to transmit the patient data back to the physician.

The spatial orientation of the physician's HCU 100 with respect to the patient's body is also tracked by the computer software. Movements of the HCU 100 can be translated and sent to the PEM 200 or 400 to simulate movement of the hand across the patient's body. In addition, an anatomy database can be incorporated to provide cross-sectional anatomy and three-dimensional renderings of the specific body area being examined.

The software translates the physical pressure response applied by the physician to the HCU 100 into an electrical signal. Standardization, calibration, and real-time monitoring of the signal and signal strength are typical program functions. The software is also responsible for the transmission protocols for electrical signal conversion and transmission from the HCU 100 to the PEM 200 or 400, and vice versa. Transmission protocols include signal transmission over land-based and non-land-based communications platforms. All pump and valve commands, including pump chamber pressurization, calibration and conversion of the transmitted electrical signal back into the appropriate pressurization command correlating with a magnitude equivalent to the actual pressure applied at the hand control unit, and selected valve on/off status are also controlled by the device software.

Figure 9:
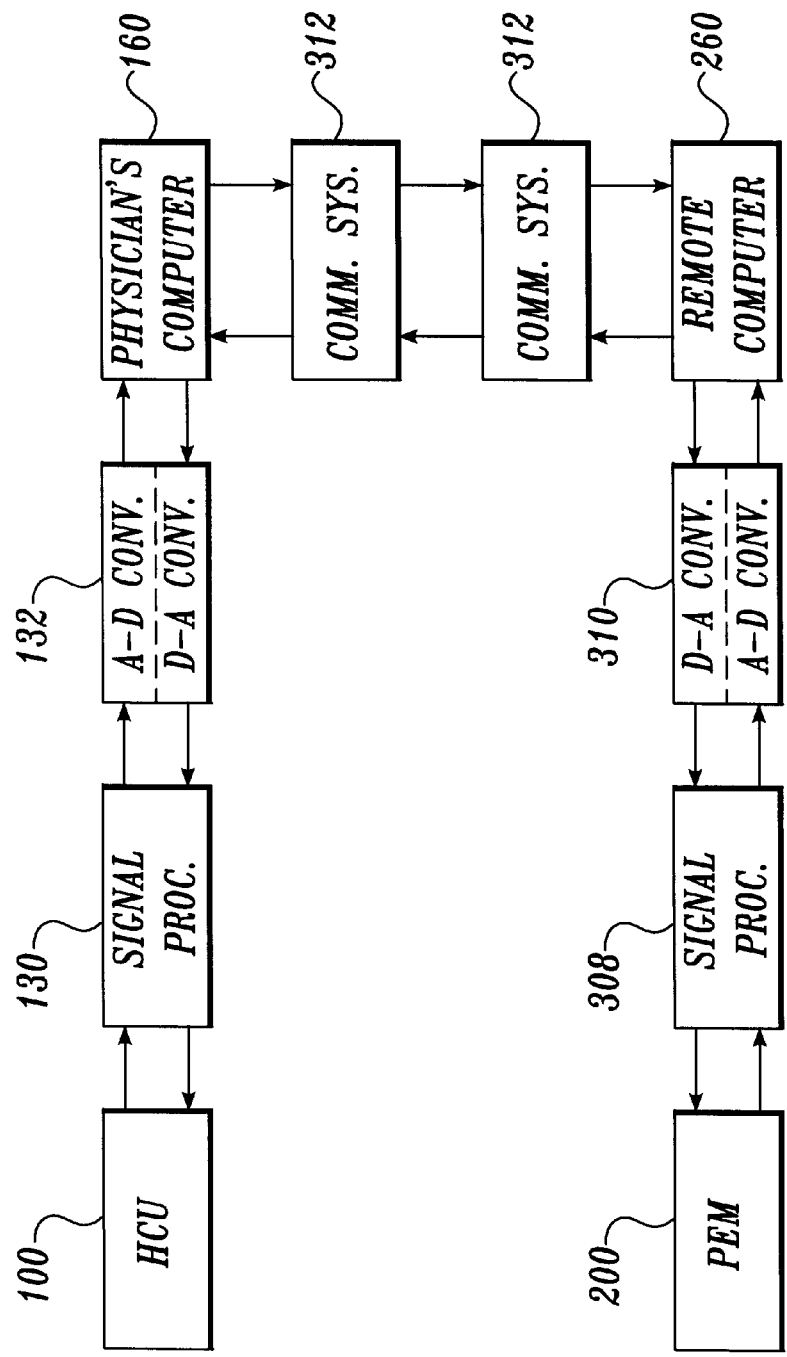
FIG. 9 is a general process flow diagram of a preferred embodiment of the present invention.

FIG. 9 represents the general process flow diagram of device functions for both the electromechanical and pneumatic/hydraulic embodiments of the present invention. Using the HCU 100, the physician selects the area of interest underlying the cells 204 or 404 to be activated corresponding to the area to be manually examined. Applying pressure to the HCU 100 via the sensory modulation subunits 140 generates signals that are sent through a signal processor 130 and analog-to-digital converter 132 to a physician's computer 160 that, in turn, sends a computer command to activate the PEM's 200 or 400 sensory modulation subunits 240 or 440 underlying the area of interest to which the HCU 100 pressure signals will be directed. The pressure transducers 244 or 444 corresponding to the area of the patient the user wishes to "feel" after the pressure stimulus is applied are then activated. This command activates the receiving cell's pressure transducers 244 or 444 so the output signal can be transmitted back to the physician's HCU 100.

The physician then presses directly on the sensory modulation subunits 140 of the HCU 100 using any combination of fingertips, proximal palmar, and distal palmar hand surfaces (ranging from a single fingertip to the whole palmar hand surface) to generate the desired input pressure stimulus equal to the force he or she would normally apply during manual examination of a patient. The applied force will vary between individuals, circumstances, and the patient areas being examined. The pressure applied by the physician against the sensory modulation subunits 140 of the HCU 100 is sensed by the pressure transducer 144 and translated into an electrical output signal. The electrical output signal is sent to the signal processor 130 and the processed analog electrical signal is converted to a digital signal 132. The digital signal is then input to a physician's computer 160.

At the physician's computer 160 the software program is responsible for software commands for linked system pathways between the various send and receive portions of the HCU 100 and the PEM 200 or 400; calibration of the signal processors 130, 308, pressure transducers 144, 244, 444, piston resistors 148, and variable pressure-producing devices 248 for both the user side and patient side equipment, and conversion of the HCU 100 electrical input signal into a corresponding PEM 200, 400 electrical output signal. If a pump system is used for the PEM 400, a pressure sensor (not shown) within the medium pressurizing reservoir 418 will be calibrated. The physician's computer 160 transmits the PEM 200, 400 electrical signal and associated software commands to the remote computer 260 via the communication systems 312. Alternatively, the patient side, or remote side, may utilize a free standing command control box 300, located near the PEM 200 or 400. The digital pressure generating signal is then converted back to an analog electrical signal 310 by a digital to analog converter, post-processed 308, then relayed to the appropriate, preselected pressure generating device of the PEM 200 or 400. The PEM 200 or 400 then applies a directed force to the patient that is based on the force applied by the user or physician to the HCU 100.

For the PEM 400, the software is responsible for receiving the incoming electrical signals from each active area of the HCU 100, assessing the corresponding magnitude of each of the input pressures applied to the various portions of the HCU 100 and converting this information into a specific pump command. The pressure commands are then transmitted to either a remote computer 260 at the patient's remote location, or directly to the command control box 300 portion of the PEM 400 previously described. The PEM 400 would then activate the pumping mechanism and pressurize the pressurizing chamber 418 in order to achieve an output pressure equal to the pressure directly applied by the physician to the HCU 100. The internal pressure of the chamber 418 is monitored by a pressure sensor that provides continuous feedback regarding the need to continue or discontinue pumping until the desired input pressure is achieved. The pressurized medium in the pressurizing chamber 418 is then transmitted to each of the selected cells 404 with open pressure valves 414 via the inlet/outlet line 410. The pressurized medium then flows into the selected cells 404 and increase the cell volume and internal cell pressure corresponding to the force applied by the physician at the HCU 100.

The downward force applied to the patient by either PEM 200 or 400 will elicit a counter-response from the patient ranging from no resistance at all and further indentation of the area being examined to great resistance or "guarding." This resistance from the patient in response to the applied force from the activated cells will be detected by the cell pressure transducer 244 or 444.

The mechanical resistance response detected by the activated pressure transducer 244 or 444 of the PEM 200 or 400 is converted into an electrical signal which is transmitted back to the command control box 300 or the remote computer 260 at the patient's location. As previously described for the input command set, this analog electrical signal will be processed 308 and converted to a digital signal 310. This digital signal is then transmitted back to the physician's computer 160 via the communications systems 312. As previously described for the HCU 100 output signal, the software program is responsible for receiving the incoming digital electrical signal(s) from each active area of the PEM 200, 400, assessing the corresponding magnitude of each of the PEM 200, 400 output pressures, and converting them into equivalent digital HCU 100 resistance signals. The digital signals are then converted to an equivalent analog electrical signal 132, post-processed 130, then directed to the appropriate preselected piston resistors of the HCU 100. The output resistance produced by the piston resistors 148 at the HCU 100 is equal to response pressure produced by the patient in response to the HCU 100 input pressure stimulus.

The counter-resistance provided by the piston resistor 148 will provide the physician with a tactile simulation of the patient's response to pressure applied over the selected area of the patient's anatomy. The system is real-time and dynamic such that the physician may simulate press-release or press-partial release maneuvers on a continuous basis within the region of preselected cells. The three key components of the device: the physician hand control unit, the computer software, and the patient examination module provide a system for a continuous, real-time, action-reaction feedback loop. It is the differential resistance between the physician's applied pressure and the patient's resistive response perceived by the physician's hand against the hand control unit that the physician can then interpret and use for medical decision-making.

Figure 10A:
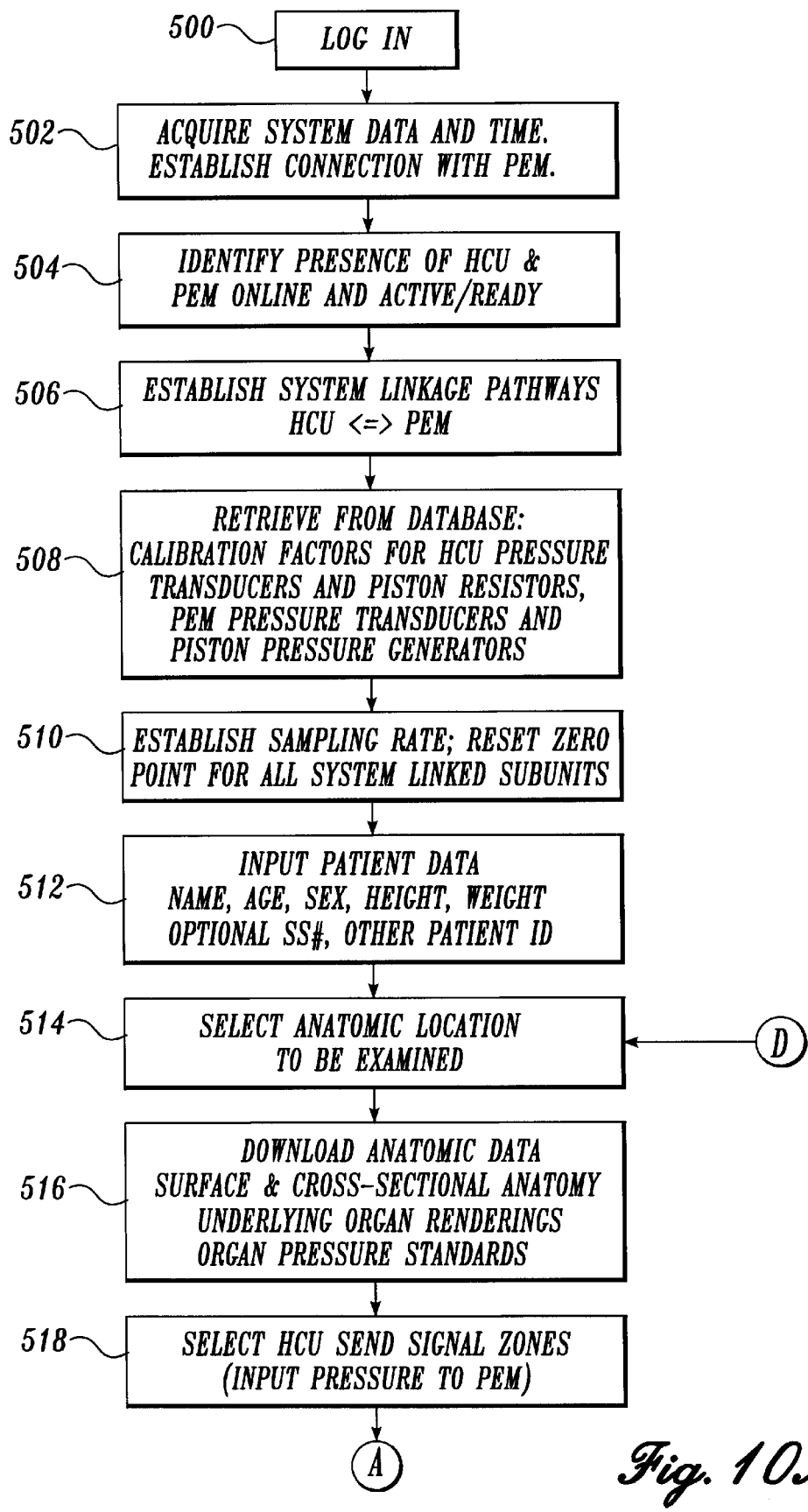
FIGS. 10A–10C present a flow diagram detailing the functions of the software controlling the preferred embodiment shown in FIG. 1.
Figure 10B:
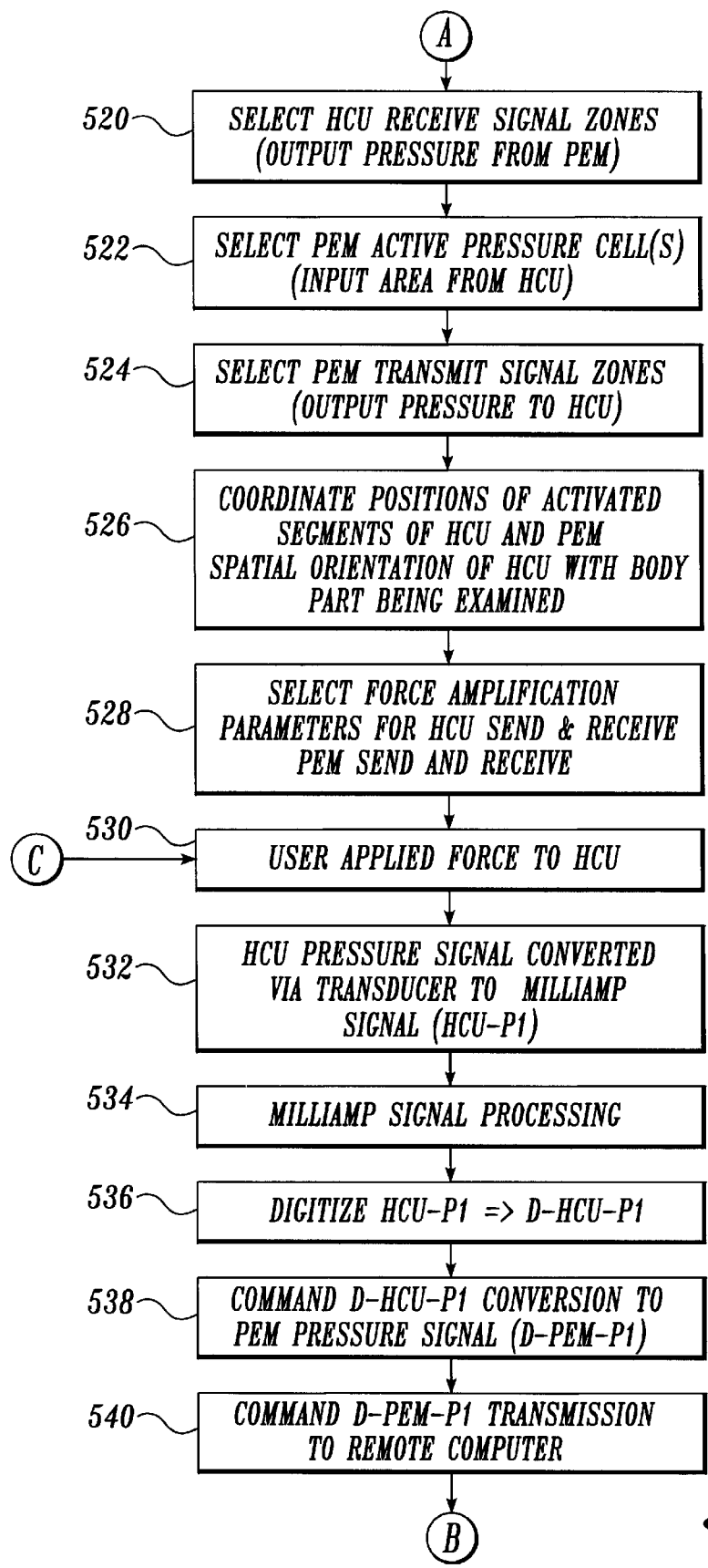
Figure 10C:
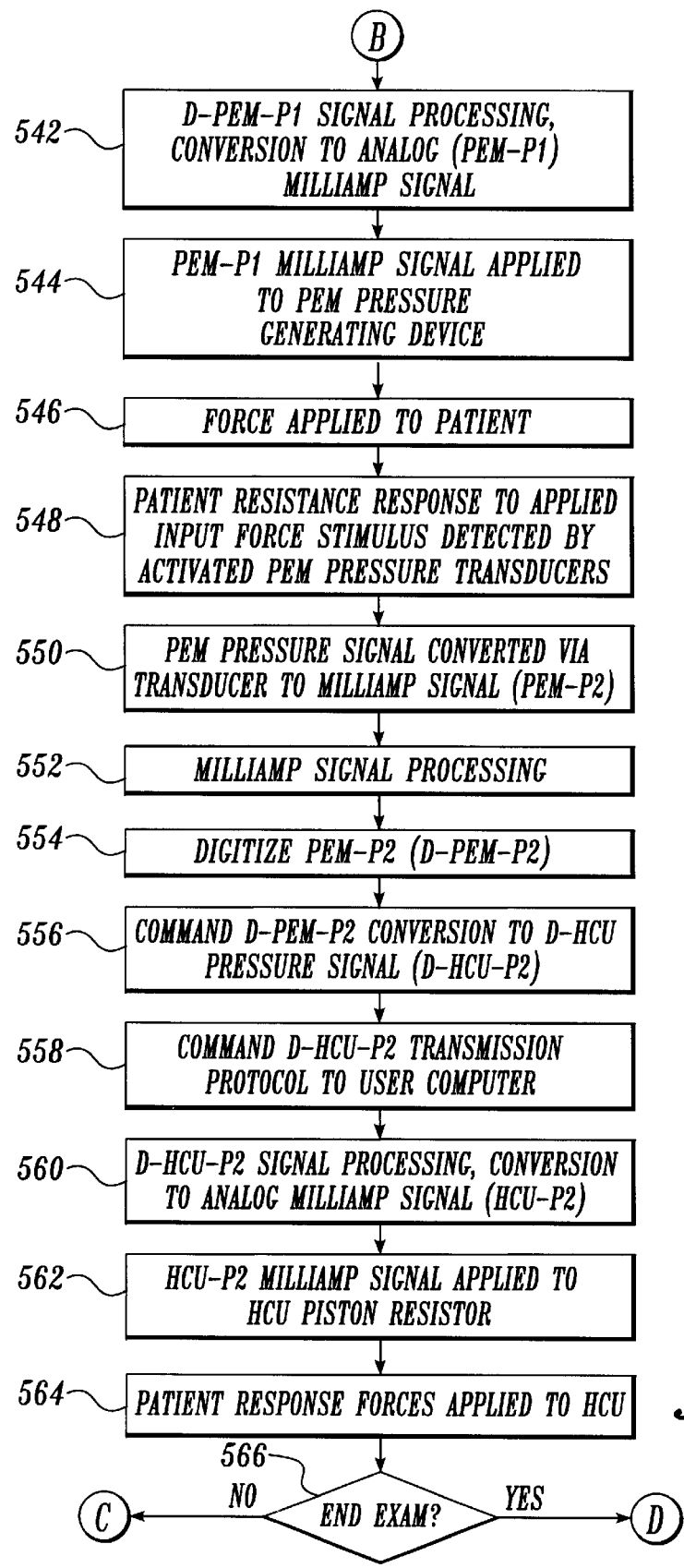

A flow chart showing the overall process that will be controlled by the software in the preferred embodiment is diagrammed in FIGS. 10A–10C. The user, generally the physician, first logs into the system 500. A mechanism for logging in is provided by any conventional means, including for example a biometric scanner in the HCU (ie., a fingerprint reader, not shown) or a more conventional requester for a user identification and password may be provided at the physician's computer 160. The software then queries for the system date and time 502, establishes a connection with the PEM and checks the status of the HCU and PEM 504, then establishes the necessary communications links 506 therebetween. In the preferred embodiment, a first database is accessed 508 by the physician's computer 160 to obtain the various calibration factors for the HCU and PEM components, such as the pressure transducers and pressure producing devices (linear actuators). Various other initiation functions are then performed by the software 510, which functions may include establishing the sampling rates for the pressure transducers and initiating and calibrating the components (for example, establish the "zero pressure" level for the pressure transducers).

Patient identification and biometric information may then be input 512, both to verify the identity of the patent for the medical records and to establish baseline parameters that may be helpful to the examination, such as the general size and age of the patient. The physician then selects the anatomical location to be examined 514. In the preferred embodiment, a database of anatomical data is accessed 516, which may include generic still or animated pictures of the portion of the anatomy that is to be examined. It is contemplated that embodiments of the present invention may use the patient medical and biometric information, in addition to generic information relating to the portion of the anatomy that is to be examined, to adjust various system parameters, such as the sensitivity of the pressure transducers and linear actuators. The physician then selects the portions of the HCU that will provide output signals to the PEM 518, the portions of the HCU that will receive feedback pressures from the PEM 520, the cells of the PEM that will receive the pressure signals from the HCU 522, and the cells of the PEM that will send pressure signals back to the HCU 524. It is anticipated that in most applications there will be a one-to-one correspondence between the active HCU portions, and the activated PEM cells, for example, that the HCU sensory modulation subunits will send and receive pressure signals to and from the same PEM cells. However, the ability to disassociate the send and receive signals is believed to provide additional functionality to the system. The present invention contemplates systems wherein it is not possible to disassociate the HCU input and output pressure signals.

The software can also coordinate the position of the activated segments of the HCU with the PEM 526, such that movement of the HCU, in a manner similar to moving a mouse, is tracked by the system to make a corresponding change in the PEM cells that are activated. Prior to the application of any force to the system, predetermined force alteration functions can be applied 528, such as force amplification/magnification or reduction/minimization of the HCU and PEM output signals. Forces are applied to the HCU 530 by the user, and the pressure signals generate low-amperage signals 532 in the pressure transducers 144 (HCU-P1), that are sent to the signal processor to produce corresponding higher-amperage signals 534, and then converted to digital signals 536 (D-HCU-P1). The D-HCU-P1 are used to generate digital pressure signals for the PEM 538 (D-PEM-P1), and transmitted 540 from the physician's computer 160 to the remote computer 260. The D-PEM-P1 pressure signal is then converted to a low amperage analog signal (PEM-PI) 542, that is applied to the variable pressure producing device 248 of the PEM, and a corresponding force is applied to the patient 546.

The patient resistance response is detected by the selected PEM cell 548, producing a pressure response signal (PEM-P2) 550, that is processed to produce a higher amperage signal 552 and digitized (D-PEM-P2) 554. The D-PEM-P2 pressure signal is used to generate a corresponding digital pressure signal for the HCU 556, transmitted from the remote computer to the physician's computer 558, and converted to an analog signal 560 that is provided 562 to the appropriate HCU piston-type variable resister 148 to produce a responsive force at the HCU. If the examination is complete 566, then the system will reset to allow the physician to begin another exam of a different part of the patient's anatomy. Otherwise the physician can apply additional forces and detect additional responses from the patient.

Although the process has been described in terms of the preferred embodiment, it will be obvious to one of ordinary skill in the art that variations on the above process are possible. For example, an embodiment may be possible wherein the pressure signals from the pressure transducers are usable, without pre-processing to a higher amperage, or pressure transducers may be used with integral A-D converters whereby a digital signal is produced directly. Optionally, the HCU and PEM may be connected directly to a common computer or a specialized data processing system for applications where the user and the patient are in close proximity. The invention can clearly be practiced without the additional functionality provided by an anatomical database. Additionally, it will be clear to one of ordinary skill in the art how the process flow shown in FIGS. 10A–10C would be modified to accommodate the hydraulic or pneumatic embodiments of the PEM described above.

Additional Applications

While the original intent of the HCU 100 is to simulate a physical examination of a patient in a remote location, applications within the field of medicine would include the ability to examine a patient in hostile environments such as deep sea, space, battlefield conditions, remote locations, and/or mountain/jungle expeditions. The present invention may also be adapted for non-medical and/or recreational usages, where it is desirable for an individual to examine, feel, or otherwise elicit a tactile response from another individual, body or object in a remote location.

Portable versions could also be applied in a medical station within the workplace, obviating the necessity of a patient having to actually leave work and traveling to a physicians office. This is very inefficient for both the patient and the physician.

It is also contemplated that with the growing use of robotic tools for performing operations, that the above-described invention could be modified in a straightforward manner to provide a physician with tactile feedback while performing an operation using a robotic system.

Portable versions could also be applied in the home where some evaluations could preclude the need for after-hours trips to the emergency room. This efficiency would have a significant effect on overall health care costs.

Any application requiring tactile information or three-dimensional tactile modeling of a physical structure required by an individual in a non-contiguous location is also within the scope of the present invention.

The present invention could also be adapted to enhance the ability of the visually impaired to communicate or feel objects without actual direct physical contact between the object and the blind individual.

While the preferred embodiment illustrated and described provides for external examination of a patient, it should be understood that the PEM could be alternately configured for use within a body cavity or incision.

The embodiments of the invention in which an exclusive property or privilege is claimed are defined as follows:

1. A device for remotely conducting a direct manual examination of a patient comprising a hand control unit, a patient examination module, and a computer, wherein said patient examination module and said hand control unit are operatively linked to said computer and are each capable of generating a force in response to an input signal and of generating an output signal in response to a detected force, wherein said hand control unit includes at least one sensory modulation subunit comprising a slab of elastic material having an embedded pressure transducer, wherein said slab of elastic material is attached to a single channel piston-type variable resistor.

2. The device of claim 1, wherein said hand control unit further comprises means for selectively interacting with said computer.

3. The device of claim 2 wherein said means of selectively interacting with said computer comprises a tracking ball and a button.

4. The device of claim 1, wherein said hand control unit has a hand-shaped upper surface and further comprises a forward portion and a rearward portion, said forward and rearward portions being slidably connected whereby said hand control unit can be adjusted to accommodate different-sized hands.

5. The device of claim 4 wherein said hand-shaped upper surface comprises four fingertip portions, each containing at least one sensory modulation subunit, a distal palmar portion containing at least one sensory modulation subunit, and a proximal palmar portion containing at least one sensory modulation subunit.

6. A device for remotely conducting a direct manual examination of a patient comprising a hand control unit, a patient examination module, and a computer, wherein said patient examination module and said hand control unit are operatively linked to said computer and are each capable of generating a force in response to an input signal and of generating an output signal in response to a detected force, wherein said patient examination module comprises:

(a) a pad removably attachable to said patient, said pad comprising a plurality of expandable cells attached to a backing, said pad including means for attaching said pad to said patient;

(b) a plurality of pressure transducers attached to said plurality of expandable cells, said pressure transducers being adapted to generate a signal that is directly related to an interface pressure between said pad and said patient; and (c) a fluid media that can be selectively directed to some of said plurality of expandable cells to produce a desired pressure within said expandable cells.

7. The device of claim 6 wherein said fluid media is air.

8. The device of claim 6 wherein said fluid media is an hydraulic fluid.

9. The device of claim 6 further comprising a p lurality of electrically actuated valves, each valve located between one of said plurality of expandable cells and a pressurized fluid media reservoir.

10. The device of claim 9 further comprising a command control box having a controller electrically connected to said plurality of valves and to said plurality of pressure transducers.

11. The device of claim 6 wherein said hand control unit comprises:

(a) a computer input device operatively linked to said computer, wherein a user can select one or more cells of said patient examination module;

(b) at least one sensory modulation subunit comprising a sensor capable of detecting pressure applied by said user to said sensor, said sensor operatively linked to said computer and said sensor producing a signal proportional to said detected pressure; and (c) a piston capable of exerting a force detectable by said user, said piston operatively linked to said computer, wherein said exerted force is responsive to said signal generated by said patient examination module.

12. The device of claim 11 wherein said sensory modulation subunit comprises a linear actuator connected to said backing and a pressure transducer located between said linear actuator and said patient.

13. The device of claim 12 further comprising a command control box having a controller electrically connected to said sensory modulation subunit.

14. A device for simulating tactile interactions with a remote body, the device comprising:

(a) a hand control unit having at least one sensory modulation subunit;

(b) an examination subunit disposed remotely from said hand control unit, said examination subunit having a plurality of sensory modulation subunits, said examination subunit being adapted to wrap around at least a portion of the remote body; and (c) means for operatively connecting at least one sensory modulation subunit of said hand control unit to at least one sensory modulation subunit of said examination unit such that a force applied to one connected sensory modulation subunit will cause a corresponding force to be exerted by the other connected sensory modulation subunit.

15. The device of claim 14 wherein said sensory modulation subunits comprise at least one pressure transducer and at least one variable pressure producing device.

16. The device of claim 14 wherein said means for operatively connecting said sensory modulation subunits comprises at least one computer and a communications system that operatively connects said hand control unit sensory modulation subunits and said examination module sensory modulation subunits to the computer.

17. The device of claim 14 wherein said hand control unit further comprises a means for selecting said at least one sensory modulation subunit of said examination module that will be operatively connecting with said at least one sensory modulation subunit of said hand control unit.

18. The device of claim 17 wherein said selecting means comprises a trackball disposed on a bottom of said hand control unit and a button disposed on an upper portion of said hand control unit.

19. A method of tactilely examining a body comprising:

(a) wrapping a portion of said body in an examination module having a plurality of sensory modulation subunits;

(b) operatively connecting at least one of said sensory modulation subunits of said examination module to at least one sensory modulation subunit on a remotely disposed hand control unit; and (c) manually applying a force to said at least one sensory modulation subunit on said hand control unit to produce a corresponding force at said connected sensory modulation unit of said examination module and detecting a feedback force from said examination module.

20. The method of claim 19 further comprising the step of remotely selecting at least one of said plurality of sensory modulation subunits of said examination module that will be operatively connected to the at least one sensory modulation subunit of said hand control unit.

21. The method of claim 19 wherein the step of operatively connecting the examination module to the hand control unit comprises the steps of transmitting signals between the examination module and the hand control unit over a global telecommunications system.

22. A method of tactilely examining a body comprising:
  (a) wrapping a portion of the body in an examination module having a plurality of sensory modulation subunits that can generate an output signal in response to an applied force and simultaneously exert a force in response to a received input signal;
  (b) connecting the examination module to a first communications system that can send and receive the input and output signals;
  (c) connecting a hand control unit having at least one sensory modulation subunit that can generate an output signal in response to an applied force and simultaneously exert a force in response to a received input signal to a second communications system that can communicate with the first communications system;
  (d) operatively connecting the first communications system with the second communications system such that the hand control unit output signals are received by the examination module and the examination module output signals are received by the hand control unit; and
  (e) applying a series of forces to the hand control unit sensory modulation subunits with a hand such that forces exerted by the hand control unit sensory modulation subunits resulting from the received output signals from the examination unit are detected.

23. A device for remotely conducting a direct manual examination of at least a portion of a body, the device comprising:
  (a) a hand control unit having a first sensory modulation subunit;
  (b) a patient examination module having a plurality of second sensory modulation subunits that are disposed in a flexible pad; and
  (c) a means for selectively operatively connecting the first sensory modulation subunit to one or more of the plurality of second sensory modulation subunits, such that an output signal from the first sensory modulation subunit is received by one or more of the second sensory modulation subunits and an output signal from one or more of the second sensory modulation subunits is received by the first sensory modulation subunit.

24. The device of claim 23, wherein the means for selectively operatively connecting the first sensory modulation subunit to one or more of the plurality of second sensory modulation subunits comprises a first computer that interfaces with the hand control unit, a second computer that interfaces with the patient examination module, and a data communications system operatively connecting the first computer with the second computer.

25. The device of claim 24, wherein the data communications system operates over standard telephone lines.

26. The device of claim 24, wherein the data communications system operates over a global telecommunication system.

27. The device of claim 24, wherein the data communications system operates over a fiber optic network.

28. A device for remotely conducting a direct manual examination of a patient comprising:
  (a) a hand control unit having at least one first sensory modulation subunit that:
    (i) detects a force applied to the first sensory modulation subunit and generates a first signal in response to the detected force, and
    (ii) exerts a force in response to a received second signal; and
  (b) a patient examination module, the patient examination module having a plurality of second sensory modulation subunits that are selectively connectable to the first sensory modulation subunit, such that:
    (i) the second sensory modulation subunits receives the first signal and exerts a force in response to the received first signal, and
    (ii) detects a force resisting the exerted force and generates the second signal based on the detected resisting force, the second signal being received by the first sensory modulation subunit.

29. The device of claim 28, wherein the plurality of second sensory modulation subunits in the patient examination module are disposed in a flexible pad.

30. The device of claim 29, wherein the patient examination module is adapted to be wrapped around at least a portion of the patient.

* * * * *

UNITED STATES PATENT AND TRADEMARK OFFICE
CERTIFICATE OF CORRECTION

PATENT NO. : 6,491,649 B1
DATED : December 10, 2002
INVENTOR(S) : M.P. Ombrellaro It is certified that error appears in the above-identified patent and that said Letters Patent is hereby corrected as shown below:

Title page,
Item [56], References Cited, U.S. PATENT DOCUMENTS, "Reinhold et al." should read -- Reinbold et al. --
Item [57], ABSTRACT,
Line 17, "pressure's" should read -- pressures --

Column 15,
Lines 19 and 25, "claim 1," should read -- claim 1 --
Line 58, "media is an" should read -- media is a --
Line 60, "p lurality" should read -- plurality --

Column 18,
Line 7, "claim 23," should read -- claim 23 --
Lines 15, 17 and 20 "claim 24," should read -- claim 24 --
Line 36, "subunits receives" should read -- subunits receive --
Line 43, "claim 28," should read -- claim 28 --
Line 46, "claim 29," should read -- claim 29 --

Signed and Sealed this

Third Day of June, 2003

JAMES E. ROGAN
*Director of the United States Patent and Trademark Office*